United States Patent [19]

Spiers et al.

[11] Patent Number: 5,916,573
[45] Date of Patent: Jun. 29, 1999

[54] TOPICAL TREATMENT OF THE SKIN WITH A GRAPESEED OIL COMPOSITION

[76] Inventors: Samantha M. Spiers, 1619B Country Club Dr., Crawfordsville, Ind. 47933; Frederick T. Cleaves, 4519-F Lawndale Dr., Greensboro, N.C. 27455

[21] Appl. No.: 08/699,238

[22] Filed: Aug. 19, 1996

Related U.S. Application Data

[60] Provisional application No. 60/002,553, Aug. 21, 1995, abandoned.
[51] Int. Cl.$^6$ ........................................ A61K 7/48
[52] U.S. Cl. .................. 424/401; 424/195.1; 424/451; 514/561; 514/567; 514/844; 514/846
[58] Field of Search ................. 424/401, 195.1, 424/451; 514/561, 567, 844, 846

[56] References Cited

U.S. PATENT DOCUMENTS 4,488,564  12/1984  Grollier et al. ............... 132/7
5,254,585  10/1993  Desjonqueres .......... 514/552

FOREIGN PATENT DOCUMENTS

4125558A1  of 1992  Germany .
4125560A1  of 1992  Germany .
4125561A1  of 1992  Germany .
4125562A1  of 1992  Germany .

*Primary Examiner*—Jyothsan Venkat
*Attorney, Agent, or Firm*—Rhodes, Coats & Bennett, L.L.P.

[57] ABSTRACT

A grapeseed oil composition for topical application to the skin comprising: a) about 1 to about 99% by weight of grapeseed oil; b) at least one hydrating agent; and c) water. Hydrating agents include vegetable glycerin, aloe-vera, and vegetable oils other than grapeseed oil, for example, vitamin E oil, jojoba oil, flaxseed oil, primrose oil and any other botanical oil. The grapeseed oil composition may further include at least one amino acid, for example, lysine and tyrosine.

5 Claims, No Drawings

5,916,573

TOPICAL TREATMENT OF THE SKIN WITH A GRAPESEED OIL COMPOSITION

This application claims the benefit of U.S. provisional application Ser. No. 60/002,553, filed Aug, 21, 1995 now abandoned.

FIELD OF THE INVENTION

The present invention relates generally to the treatment of skin with an antioxidant, and more particularly to the treatment of skin with a topical grapeseed oil composition.

BACKGROUND OF THE INVENTION

Natural plant oils have long been used in a variety of applications. For example, U.S. Pat. No. 4,488,564 (Grollier et. al.) discloses an oily composition intended for the treatment of keratin substances in particular human hair and skin. Vegetable oils including grapeseed oil are among the suitable components for the oily compound.

U.S. Pat. No. 5,254,585 (Desjonqueres) discloses the use of peroxidated lipids such as natural vegetable oils like grapeseed oil to treat circulatory insufficiencies.

DE 4125558A1, DE 4125560A1, and DE 4125562A1 disclose the use of plant oils including grapeseed oil in the treatment of aromatherapy.

Grapeseed oil is known to contain powerful antioxidants. Antioxidants inhibit the production of free-radicals, which are created during an oxidation process initiated by ultraviolet radiation. Of great concern is the alarming increase in deadly skin cancers caused by prolonged exposure to ultraviolet radiation. Further, it is known that free-radicals negatively impact on the ability of natural body lipids to maintain proper moisture levels.

The human body provides some natural antioxidant protection to the skin through normal blood flow. However, poor dietary habits often lead to inadequate blood flow through the tiny blood vessels of the skin, particularly near the surface. As a result, blocking of essential nutrition to the skin occurs.

To combat the effects of ultraviolet radiation on the skin's collagen, antioxidants in the form of extracted oligomeric proanthrocyanidins have been shown to produce beneficial effects to the skin under laboratory conditions. However, widespread use of extracted oligomeric proanthrocyanidins has been impractical, since extracted oligomeric proanthrocyanidins cannot be easily incorporated into creams or lotions for topical application. The difficulty of such incorporation is due to the fact that extracted oligomeric proanthrocyanidins hydrate very quickly when contacted with water and aqueous solutions. Upon hydration, extracted oligomeric proanthrocyanidins lose most of their antioxidant properties. As a result, extracted oligomeric proanthrocyanidins lack the stability that is necessary to sustain their antioxidant properties and the benefits derived therefrom. To overcome the disadvantages associated with extracted oligomeric proanthrocyanidins, a more stable form of this antioxidant is needed.

SUMMARY OF THE INVENTION

It has been discovered that an oily composition containing grapeseed oil when applied topically to the human skin provides the beneficial antioxidant properties of the grapeseed oil to the outermost skin layers. The grapeseed oil used in the present invention is obtained from grapeseeds, a plant source which contains the highest percentage of oligomeric proanthrocyanidins available, typically greater than 90%. The oligomeric proanthrocyanidins are not extracted but, rather, exist in their natural state. As a result, the oligomeric proanthrocyanidins contained in the grapeseed oil composition exhibit high stability not heretofore known.

In accordance with the present invention, the skin treatment comprises an oily composition comprising approximately 1% to about 99% grapeseed oil as the primary antioxidant component; at least one hydrating agent; and deionized water. Suitable hydrating agents, which facilitate cell rehydration, include vegetable glycerin, aloe-vera, and vegetable oils other than grapeseed oil, for example, vitamin E oil, jojoba oil, flaxseed oil, primrose oil or any other botanical essential oils. The preferred concentration range of the hydrating agent is between about 30 and about 60% by weight. Deionized water is in a concentration from about 10 to about 20% by weight.

The grapeseed oil composition may further include at least one amino acid, for example, lysine and tyrosine. It has been found that the addition of amino acids to the composition enhances the overall penetration of the composition into the skin. The amino acids, when present, are typically in an amount ranging between about 0.1 and about 0.5% by weight.

The grapeseed oil composition, when applied topically, is generally in the form of an oil, a cream, a lotion, a gel, a capsule, or any combination thereof. If desired, a botanical fragrance oil may also be included in the composition such as lavender, sandalwood, and geranium oils.

Results from the topical application of the grapeseed oil containing composition suggest that the composition repairs the free-radical damage associated with exposure to ultraviolet radiation as well as enhances the natural ability of human body lipids to maintain proper levels of moisture. The studies further suggest that the topical use of the grapeseed oil composition is both safe and effective.

These and other aspects of the present invention will become apparent to those skilled in the art after reading the following description of the preferred embodiments.

DETAILED DESCRIPTION OF THE PREFERRED EMBODIMENTS

The individual components of the topical grapeseed oil composition of the present invention are readily available from commercial sources. It is preferred that components of the highest purity be used to maximize the beneficial effects of the composition. The composition comprises about 1% to about 99% grapeseed oil (Sigg, Teaneck N.J.) in combination with at least one hydrating agent and deionized water. The hydrating agents include, but are not limited to, vitamin E oil (Solgar, Lynbrook N.Y.), jojoba oil (Now, Glendale Heights Ill.), vegetable glycerin (Now), and aloe-vera (Lilly of Desert, Irving Tex.). To enhance the penetrating effect of the composition into the skin, at least one amino acid such as tyrosine or lysine (Twinlab, Ronkonkoma N.Y.) may be added. If desired a perfume component (Oshadhi, San Juan Capistrano Calif.) may be also included.

By gentle massage, the grapeseed oil composition is applied to the skin in an oil, lotion, cream, gel or capsule form, but is not solely limited to these formulations.

In producing the composition of the present invention, the lysine and tyrosine are first dissolved in deionized water. One suggested concentration is 500 mg each of lysine and tyrosine dissolved in 1 oz. deionized water. However, the concentration of the amino acids will depend on the total volume of the composition that is desired. Generally, the amino acids and deionized water are stirred together at room temperature until thoroughly mixed. The remaining components, grapeseed oil, hydrating agents and fragrance, are then subsequently added, but not in any special sequence. The final mixture that is produced is light yellowish-sand in color. The composition may be applied to the skin as an oily composition or, in the alternative, in the form of a cream, lotion, gel, capsule or any combination thereof in an amount sufficient to cover the targeted skin area. If the oily grapeseed composition is used, it should be shaken prior to each use.

The following examples further illustrate the embodiments of the present invention:

EXAMPLE 1

The following composition was prepared and tested:

| | |
|---|---|
| Grapeseed oil | 2 oz. |
| Water | 1 oz. |
| Vegetable glycerin | 2 oz. |
| Aloe-vera | 3 oz. |
| Vitamin E oil | 0.5 oz. |
| Jojoba oil | 0.5 oz. |
| Lysine | 500 mg |
| Tyrosine | 500 mg |
| Perfume | trace amount |

In applying the composition of the present invention, the user moistened her fingertips with an amount of the composition that is sufficient to cover the targeted skin area. The composition was applied to dry clean skin. Following application, it was generally found that the skin exhibited a greater smoothness to the touch and appeared to be more hydrated. Free-radicals are known to ruin the skin's natural moisture protection. It is believed that the grapeseed oil composition's antioxidant properties allows the skin to stay moist, and may further function in preventing or repairing free-radical harm to the skin.

EXAMPLE 2

To analyze the safety and effectiveness of the grapeseed oil composition, clinical studies were conducted using six individuals, each having had the subject grapeseed oil composition applied topically to one-half of their face. Application of the composition was studied for a period of 10–30 days. The following conditions were evaluated in each of the six individuals: 1) skin hydration; 2) collagen damage (age lines and/or wrinkles); 3) scar tissue; 4) nevi; 5) presence of dark circles underneath the eyes; and 6) skin sensitivity to the composition. Using visual inspections in combination with patients acting as their own controls, moderate to excellent results were observed in all six individuals who applied the topical grapeseed oil composition. The overall results that were achieved with the grapeseed oil composition is shown below in Table I.

TABLE I

| Patient | Gender | # Days Treated | General Observations |
|---|---|---|---|
| No.1 | Female | 22 | This patient presented with the most severe case history for undergoing severe allergic reactions to most skin products including cosmetics. Typically, this patient often had to use steroid creams to treat swollen eyelids following use of most skin products. Patient exhibited scar tissue on both sides of her face. Following treatment with the grapeseed oil composition topically, patient showed no signs of allergic reaction after using the grapeseed oil for 22 days. Test side of patient's face appeared "younger" with less lines, and patient's scar tissue was much less noticeable. |
| No.2 | Female | 10 | Patient used the composition on the right side of her face for 10 days continuously, applying the composition at least once a day and twice a day for two days. Overall, patient exhibited less depth in the creases around the right side of her mouth. In addition, the previously dark circles under patient's eyes appeared much lighter under the right eye following application of the composition. |
| No.3 | Male | 30 | Patient presented a raised nevus 1/8" in diameter between his eyebrows and at the top of the bridge of his nose. The nevus was medium brown in color. Following a 30-day treatment period in which the composition was applied 20 times (not daily), the nevus turned flesh color, matching the color of the surrounding skin and decreased in size by approximately one-half. |
| No.4 | Female | 10 | The patient applied the composition for 10 days to both sides of her face. Patient's chronic dry skin condition appeared to be corrected following application of the grapeseed oil composition. Patient had a history of allergic reactions to various skin products, but had no such reaction to the grapeseed oil composition. Further, a scar, which had been present on the patient since age 10, completely disappeared following the application of the composition. |
| No.5 | Female | 8 | This patient applied the grapeseed oil composition five times over an 8-day period with two fingertips once a day. Patient reported great improvement in skin texture and skin hydration as well as fullness under the eye on the tested side of the face. |
| No.6 | Female | 10 | The patient applied the composition twice daily for five days and then once daily for five days. The composition was usually applied at bedtime. Most notably, patient observed diminishing of the dark circle under her right eye, the test application side. Creases around the right side of the mouth seemed to be plumper and less deep than the corresponding line on the left side. The fine lines over the lip area appeared less diminished. The composition was also determined to be an excellent lubricant and emollient for the lips. |

Certain modifications and improvements will occur to those skilled in the art upon a reading of the foregoing description. By way of example, it is contemplated that the grapeseed oil composition of the present invention can be modified by the addition of other constituents, which enhance the antioxidant properties of the composition and/or reverse the free-radical damage to the skin's collagen. For example, fruit acids such as alphahydroxy and glycolic acids may be added. Additionally, the following components may be included: flaxseed oil, primrose oil or any other botanical essential oils, liquid colloidal oxygen or liquid silica.

It should be understood that all such modifications and improvements have been deleted herein for the sake of conciseness and readability, but are properly within the scope of the following claims.

We claim:

1. A grapeseed oil composition for topical application to the skin comprising:
   a) about 1 to about 99% grapeseed oil;
   b) about 30 to about 60% of at least one hydrating agent;
   c) about 0.1 to about 0.5% of an amino acid wherein the amino acid include lysine and tyrosine; and
   d) about 10 to about 20% of deionized water.

2. The grapeseed oil composition according to claim 1, wherein the hydrating agent is selected from the group consisting of vegetable glycerin, vitamin E oil, jojoba oil, aloe-vera, flaxseed oil, and primrose oil.

3. The grapeseed oil composition according to claim 1, further including about <0.5% of fragrance.

4. A grapeseed oil composition according to claim 1 in the form of a cream, a lotion, a gel, a capsule, or any combination thereof.

5. A method for the topical treatment of skin with a grapeseed oil composition, to repair the free radical damage comprising the step of applying to a preselected area of skin the composition of claim 1 in an amount sufficient to cover the area.

* * * * *